(12) United States Patent
Lutnesky et al.

(10) Patent No.: US 10,591,502 B2
(45) Date of Patent: Mar. 17, 2020

(54) CASSETTES INCLUDING OVERFLOW RESERVOIRS

(71) Applicant: HEWLETT-PACKARD DEVELOPMENT COMPANY, L.P., Houston, TX (US)

(72) Inventors: Gary G. Lutnesky, Corvallis, OR (US); Dennis R. Esterberg, Philomath, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 152 days.

(21) Appl. No.: 15/477,845

(22) Filed: Apr. 3, 2017

(65) Prior Publication Data
US 2018/0284147 A1 Oct. 4, 2018

(51) Int. Cl.
*G01N 35/10* (2006.01)
*B01L 3/00* (2006.01)

(52) U.S. Cl.
CPC .... *G01N 35/1002* (2013.01); *B01L 3/502715* (2013.01); *B01L 2200/027* (2013.01); *B01L 2200/16* (2013.01); *B01L 2300/0848* (2013.01); *G01N 2035/1034* (2013.01)

(58) Field of Classification Search
CPC ............... G01N 35/1002; G01N 35/10; B01L 3/502715; B01L 3/5027; B01L 3/502; B01L 3/50; B01L 3/00
USPC .......................................... 422/502, 500, 50
See application file for complete search history.

(56) References Cited

U.S. PATENT DOCUMENTS

| | | | |
|---|---|---|---|
| 5,427,136 A | 6/1995 | Weishew | |
| 7,723,811 B2 | 5/2010 | Haluzak et al. | |
| 8,329,437 B1 | 12/2012 | Aykuffe | |
| 8,383,393 B2 | 2/2013 | Gumbrecht et al. | |
| 9,011,658 B2 | 4/2015 | Bryan | |
| 2009/0130719 A1* | 5/2009 | Handique | B01L 3/5025 435/91.2 |
| 2010/0244873 A1* | 9/2010 | Dozier, II | G01R 31/2889 324/762.03 |
| 2014/0001582 A1 | 1/2014 | Kuo et al. | |
| 2014/0193309 A1* | 7/2014 | Still | B01L 3/0268 422/500 |
| 2015/0336100 A1* | 11/2015 | Esterberg | B41J 2/1752 422/559 |

FOREIGN PATENT DOCUMENTS

WO  WO 2018/144018 A1 *  8/2018  ............... G01N 1/00

OTHER PUBLICATIONS

Chai, S.C. et al., Practical Considerations of Liquid Handling Devices in Drug Discovery, 2013, < http://cdn.intechopen.com/pdfs-wm/42006.pdf >.

* cited by examiner

*Primary Examiner* — Christine T Mui
(74) *Attorney, Agent, or Firm* — Fabian VanCott (57) ABSTRACT

A cassette may include a substrate, a die coupled to the substrate, a reservoir defined in a first side of the substrate exposing a proximal side of the die to an external atmosphere, and an overflow reservoir defined in the first side of the substrate and surrounding at least a portion of a perimeter of the reservoir.

20 Claims, 7 Drawing Sheets

CASSETTES INCLUDING OVERFLOW RESERVOIRS

BACKGROUND

An "assay run" is an investigative or analytic event used in, for example, laboratory medicine, pharmacology, analytical chemistry, environmental biology, or molecular biology, for qualitatively assessing or quantitatively measuring the presence, amount, or the functional activity of a sample. The sample may be a drug, a genomic sample, a proteomic sample, a biochemical substance, a cell in an organism, an organic sample, or other inorganic and organic chemical samples. An assay run may measure an intensive property of the sample and express it in the relevant measurement unit such as, for example, molarity, density, functional activity in enzyme international units, degree of some effect in comparison to a standard, among other measurable characteristics. An assay may involve reacting a sample with a number of reagents, and may be classified as an instance of an assay procedure conforming to an assay protocol. An assay protocol may involve a set of reagent and/or sample fluids being dispensed in specific amounts to a number of assay reaction sites such as wells within an assay plate. Further, an assay protocol may include additional processing such as mixing, separation, heating or cooling, incubation, and eventually at least one read-out. The reproducibility and run-to-run comparability of an assay depends on the reproduction of its protocol.

BRIEF DESCRIPTION OF THE DRAWINGS

The accompanying drawings illustrate various examples of the principles described herein and are a part of the specification. The illustrated examples are given merely for illustration, and do not limit the scope of the claims.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

Assay runs, as described above, have been done by hand using, for example a pipette. In order to complete the assay, a user may selectively take a sample using the pipette and eject a metered amount of the sample into individual wells of an assay plate. This is all done by hand and has proven to be relatively time consuming. Additionally, because a human is ejecting the samples into the individual wells of the assay plate, mistakes may be made and an extra amount of the sample may be added to any particular well or a portion of sample may not be added at all.

To place user interaction to a minimum, automated assay fluid dispensing systems have been developed that may dispense assay fluids, e.g., samples and reagents, in a precise, controlled fashion to multiple reaction sites within an assay plate in a short time. Some automated fluid ejection systems employ a fluid-ejection driver that uses interchangeable cassettes. The cassettes may contain the assay fluids and may be controlled so that they deposit assay fluids onto reaction sites. For example, a reaction medium may be moved relative to the cassette so that, over a relatively short time, an assay fluid may be deposited in the same or varying amounts at different reaction sites of the reaction medium.

These cassettes may be used so that single or multiple fluids can be dispensed contemporaneously. For example, multiple samples can be deposited at respective reaction sites in parallel or quickly in serial in order to reduce the time to titrate a plurality of samples. Herein, "cassette" refers to a user-replaceable component of a dispenser system, through which at least one fluid flow through, respectively, at least one fluid channel before being dispensed from the dispensing system.

During operation of the automated fluid ejection system, a reservoir may be filled with the described fluids for eventual ejection of those fluids into any number of wells within the assay plate. The introduction of the fluids into the reservoir may be one instance where a user implements a device such as a pipet to introduce the fluid within the automated fluid ejection system.

The cassette may further include a number of electrical connection pads and electrical traces defined on the surface of a substrate of the cassette. The electrical connection pads and electrical traces may be used to interface the cassette with the automated fluid ejection system. If an amount of fluid deposited into the reservoir defined in the substrate of the cassette touches or otherwise electrically connects two or more electrical pads or traces, it may short out the electronic components of the automated fluid ejection system or cassette. For example, a die coupled to the substrate of the cassette and electrically coupled to the automated fluid ejection system via the electrical traces and pads may be damaged if a portion of the fluid creates a short between two or more electrical traces or pads. Although the cassette may be meant to be disposable, damage to the die will result in a defective cassette potentially increasing costs of operation.

Still further, should any fluid accidentally cause a short between the electrical traces and/or pads, the automated fluid ejection system may be damaged. This further increases the costs of operation and may potentially irreparably damage the automated fluid ejection system.

Examples described herein provide for a cassette having a reservoir defined in the substrate of the cassette and an overflow reservoir surrounding at least a portion of the perimeter. The overflow reservoir prevents accidental overflow of the reservoir thereby preventing any fluid from reaching or otherwise coming into contact with the electrical traces and/or electrical pads. The portion of the overflow reservoir may at least be intermediate to the reservoir and the electrical traces and pads.

The present specification therefore describes a cassette that includes a substrate, a die coupled to the substrate, a reservoir defined in a first side of the substrate exposing a proximal side of the die to an external atmosphere, and an overflow reservoir defined in the first side of the substrate and surrounding at least a portion of a perimeter of the reservoir.

The present specification also describes a system that includes at least one dispense head where the at least one dispense head includes a substrate, a die coupled to the substrate, a reservoir defined within a first side of the substrate exposing a proximal side of the die to an external atmosphere, an overflow reservoir defined in the first side of the substrate and surround at least a portion of the reservoir, and a number of electrical contacts formed on the first side of the substrate.

The present specification further describes a micro electromechanical system (MEMs) device that includes a substrate having a first side and a second side, a die coupled to the second side of the substrate, a reservoir defined within a first side of the substrate exposing a proximal side of the die to an external atmosphere; and an overflow reservoir defined in the first side of the substrate and surrounding at least a portion of the reservoir.

As used in the present specification and in the appended claims, the term "a number of" or similar language is meant to be understood broadly as any positive number comprising 1 to infinity; zero not being a number, but the absence of a number.

In the following description, for purposes of explanation, numerous specific details are set forth in order to provide a thorough understanding of the present systems and methods. It will be apparent, however, to one skilled in the art that the present apparatus, systems, and methods may be practiced without these specific details. Reference in the specification to "an example" or similar language means that a particular feature, structure, or characteristic described in connection with that example is included as described, but may or may not be included in other examples.

Figure 1:
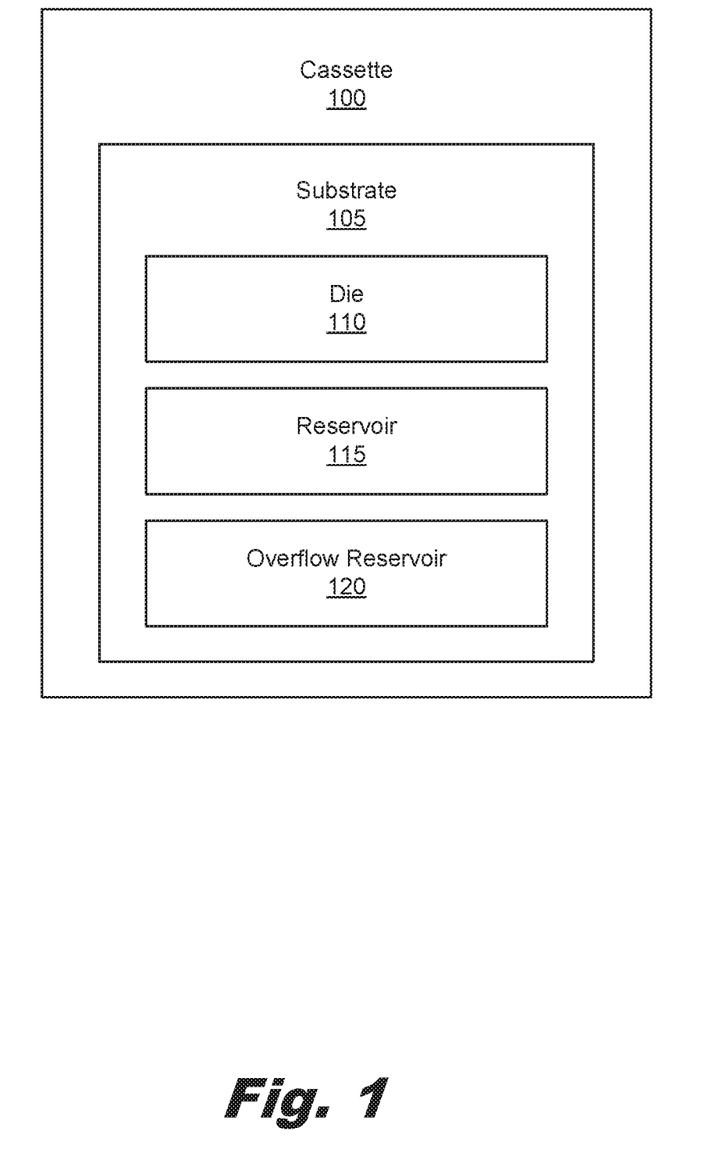
FIG. 1 is a block diagram of a cassette according to an example of the principles described herein.

FIG. 1 is a block diagram of a cassette (100) according to an example of the principles described herein. The cassette (100) may include a substrate (105). The substrate (105) may include a die (110) coupled to a side of the substrate (105), a reservoir (115) into the body of the substrate (115), and an overflow reservoir (120) also defined in the body of the substrate (115).

The substrate (105) made be made of any resilient material that allows the cassette (100) to interface with an automated fluid ejection system. In an example, the substrate (105) is made of a plastic. In an example, the substrate (105) is made of polyether ether ketone (PEEK). In an example, the substrate (105) is made of polyetherimide (PEI).

The die (110) may be any device that may eject an amount of fluid from the cassette (100). In an example, the die (110) is a silicon die. In an example, the die (110) may include any number of layers of any type of material. In an example, the die (110) may include a silicon substrate having a rear face of the silicon die being exposed to atmosphere via the slot and the reservoir (115). A fluid to be ejected from the die (110) may be placed in the reservoir (115) and, via the slot, may be provided to the die (110) for ejection of the fluid. The die (110) may further include a nozzle plate layer that includes a number of nozzles through which the fluid is ejected.

The reservoir (115) may hold any amount of fluid to be ejected from the die (110) during operation of the cassette (110). In an example, the reservoir (115) is formed into the body of the substrate (105) such that the reservoir (115) and the substrate (105) form a monolithic piece. In an example, the fluidic volume of the reservoir (115) is between 15 and 35 microliters (µL). In an example, the volume of the reservoir (115) is between 20 and 30 µL. In an example, volume of the reservoir (115) is 25 µL. In an example, the volume of the reservoir (115) is between 180 and 260 µL. In an example, the volume of the reservoir (115) is between 200 and 240 µL. In an example, the volume of the reservoir (115) is 220 µL. In an example, the volume of the reservoir (115) is between 15 and 230 µL.

Around the reservoir (115) may be formed an overflow reservoir (120). Similar to the reservoir (115), the overflow reservoir (120) may be formed into the body of the substrate (105) such that the reservoir (115), the substrate (105), and the overflow reservoir (120) form a monolithic piece. In an example, the fluidic volume of the overflow reservoir (120) is between 176 and 196 µL. In an example, the fluidic volume of the overflow reservoir (120) is between 181 and 191 µL. In an example, the fluidic volume of the overflow reservoir (120) is 186 µL. In an example, the fluidic volume of the overflow reservoir (120) is between 161 and 181 µL. In an example, the fluidic volume of the overflow reservoir (120) is between 166 and 176 µL. In an example, the fluidic volume of the overflow reservoir (120) is 171 µL. In an example, the fluidic volume of the overflow reservoir (120) is between 176 and 196 µL. In an example, the fluidic volume of the overflow reservoir (120) is between 161 and 196 µL. In an example, the fluidic volume of the overflow reservoir (120) is between 130 and 220 µL.

The overflow reservoir (120) may be formed around at least a portion of a perimeter of the reservoir (115). In an example, the overflow reservoir (120) may be disposed between the reservoir (115) and a number of electrical contacts formed on the substrate (105) of the cassette (100). As described herein, the electrical contacts allow the cassette (100) and the die (110) to interface with an automated assay fluid dispensing system. The interface between the cassette (100) and the automated assay fluid dispensing system could be shorted if the fluid used to eject from the die (110) is present on the electrical traces and/or electrical pads defined on the substrate (105). To present the fluid from contacting the electrical traces and/or electrical pads, the overflow reservoir (120) is placed between the electrical traces and/or electrical pads and the reservoir (115).

The substrate (105) may further define a wall between the overflow reservoir (120) and the electrical traces and/or electrical pads. The wall may be formed by forming a lip around a perimeter of both the reservoir (115) and overflow reservoir below an upper-most surface of the substrate (105). In an example, a two-tier level within the substrate (105) may be provided; the first level defining the lowest point in the bottom of the reservoir (115) and overflow reservoir (120) and the second level defining the lip formed around a perimeter of both the reservoir (115) and overflow reservoir (120). Both levels may fall below the upper-most surface of the substrate (105).

With or without the wall, the overflow reservoir (120) provides for a location where fluids placed in the reservoir (115) to be held should the volumetric capacity of the reservoir (115) be exceeded by a user pipetting the fluid therein. Further, because, in an example, the overflow reservoir (120) surrounds the entire perimeter of the reservoir (115), a distance between the reservoir (115) and any electrical connection pads and electrical traces may be created such that a user may pipette an amount of fluid into a reservoir (115) that is placed a distance from the electrical connection pads and electrical traces. Consequently, the user is relatively less likely to pipet the fluid directly onto the electrical connection pads and electrical traces.

In an example, a portion of the perimeter of the reservoir (115) is surrounded by the overflow reservoir (120). In this example, the overflow reservoir (120) may be disposed between the reservoir (115) and the electrical connection pads and electrical traces so as to decrease the likelihood that the user pipets an amount of fluid directly onto or near the electrical connection pads and electrical traces.

Figure 2:
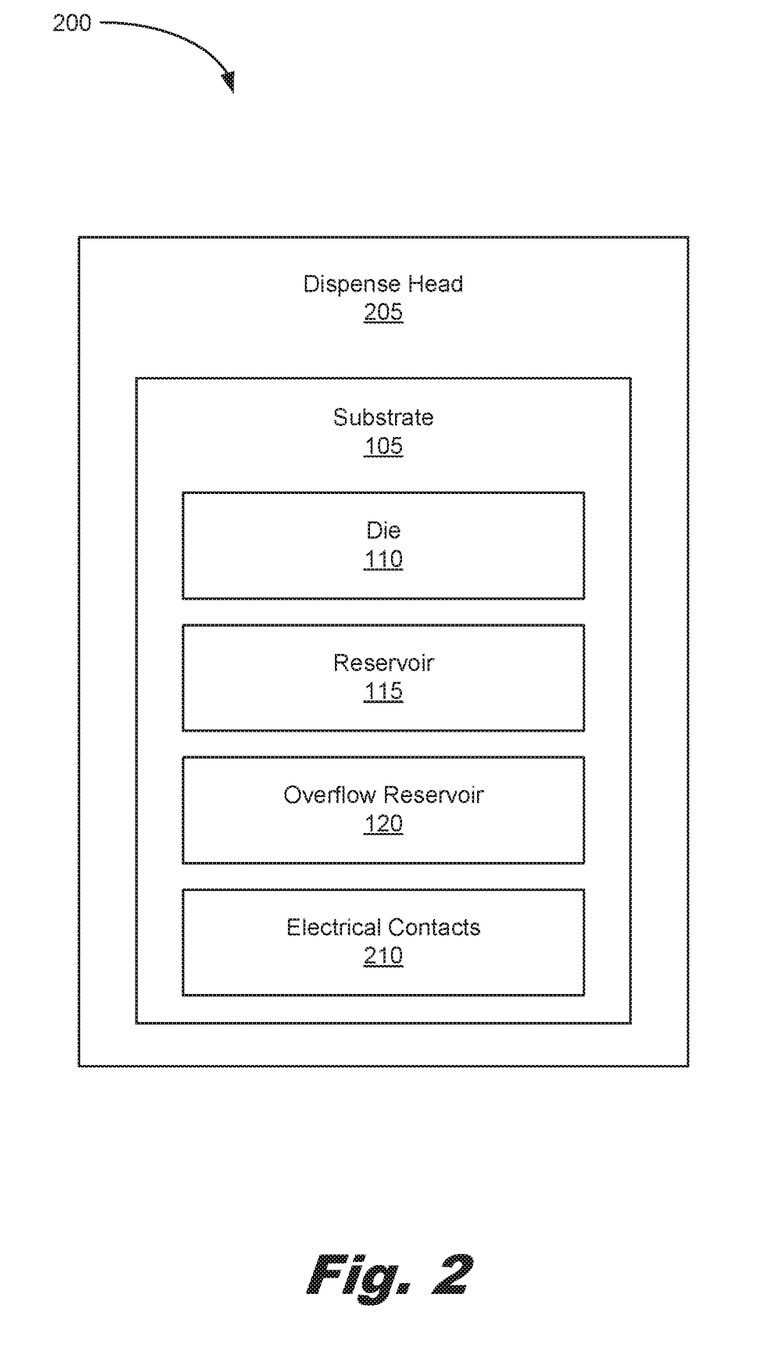
FIG. 2 is a block diagram of a system including at least one dispense head according to an example of the principles described herein.

FIG. 2 is a block diagram of a system (200) including at least one dispense head (205) according to an example of the principles described herein. In an example, the dispense head (205) may include a single substrate (105) that includes a plurality of sets of dies (110), reservoirs (115), and/or overflow reservoirs (120). In this example, multiple reservoirs (115) may be defined in the substrate (105) that may funnel or otherwise direct an amount of fluid to a respective die (110) for ejection of the fluids into an assay plate. With each reservoir (115), a respective overflow reservoir (120) may be defined around, at least partially, the perimeter of the reservoir (115). In an example, a respective overflow reservoir (120) surround the entire perimeter of its respective reservoir (115).

The substrate (105) may further include a number of electrical contacts (210) to interface the dispense head (205) with, for example, an automated assay fluid dispensing system. In an example, the number of electrical contacts (210) may include, at least, the electrical connection pads and electrical traces described herein. These electrical contacts (210) may be formed on the surface of the substrate (105) using, for example, a laser direct structuring (LDS) process. In an example, the LDS process may include doping the substrate (105) material with a metallic inorganic compound that may be activated by a laser at certain locations on the substrate (105). A metallization process such as a copper bath may then be conducted to fill in the traces made by the laser with the metallic inorganic compound acting as a nucleation point for the copper atoms to couple to.

In an example, the number of electrical contacts (210) electrically couple a single die (110) coupled to the substrate (105) to the automated assay fluid dispensing system. In this example, the number of electrical contacts (210) defined on the substrate (105) may depend on the number of electrical contacts of the automated assay fluid dispensing system and the number of electrical pads on the die (110).

In an example, the number of electrical contacts (210) electrically couple a plurality of dies (110) coupled to the substrate (105) to the automated assay fluid dispensing system. In this example, the number of electrical contacts (210) defined on the substrate (105) may depend on the number of electrical contacts of the automated assay fluid dispensing system, the number of electrical pads on each die (110), and the number of dies. In this example, the substrate (105) is said to have a plurality of dispense heads.

Figure 3:
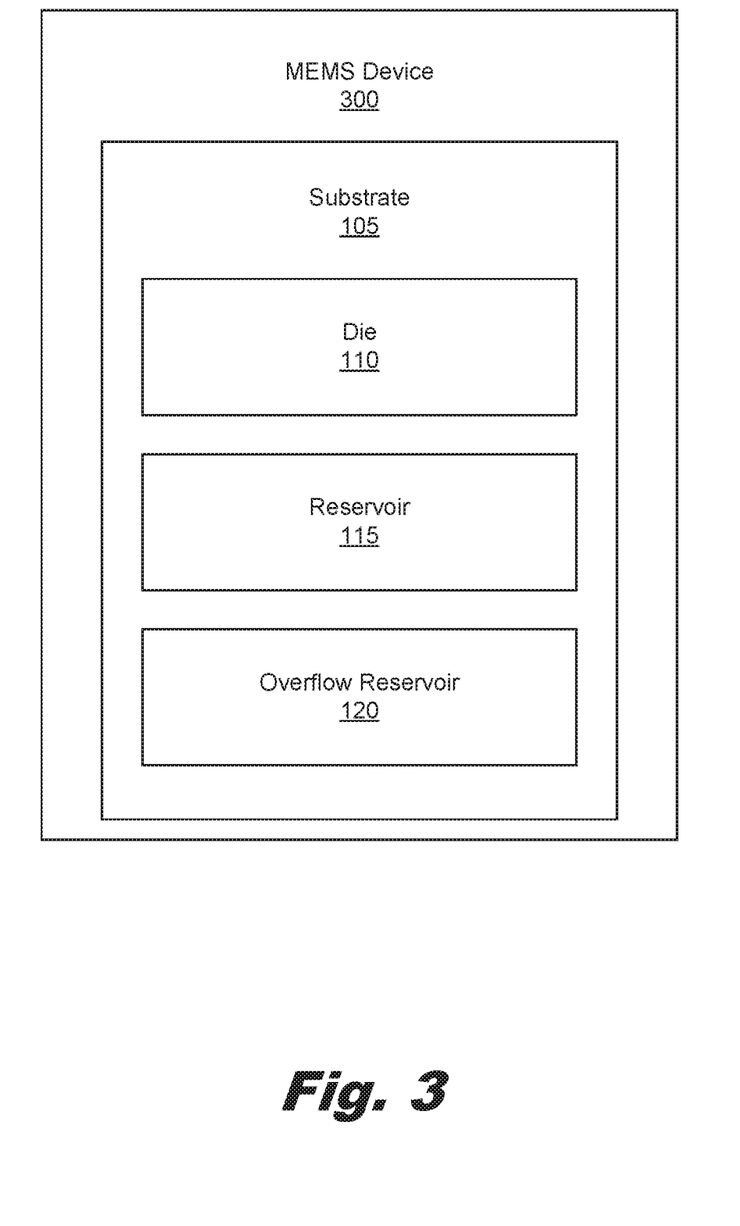
FIG. 3 is a block diagram of a micro electromechanical system (MEMs) device according to an example of the principles described herein.

FIG. 3 is a block diagram of a micro electromechanical system (MEMS) device (300) according to an example of the principles described herein. The MEMS device may include a substrate (105) having a first and opposite second side. A die (110) may be coupled to the second side of the substrate (105), A reservoir (115) may be defined within a first side of the substrate (105) exposing a proximal side of the die (110) to an external atmosphere via, for example, a slot. The MEMS device (300) may further have an overflow reservoir (120) defined in the first side of the substrate (105) and surrounding at least a portion of a perimeter of the reservoir (115).

Figure 4A:
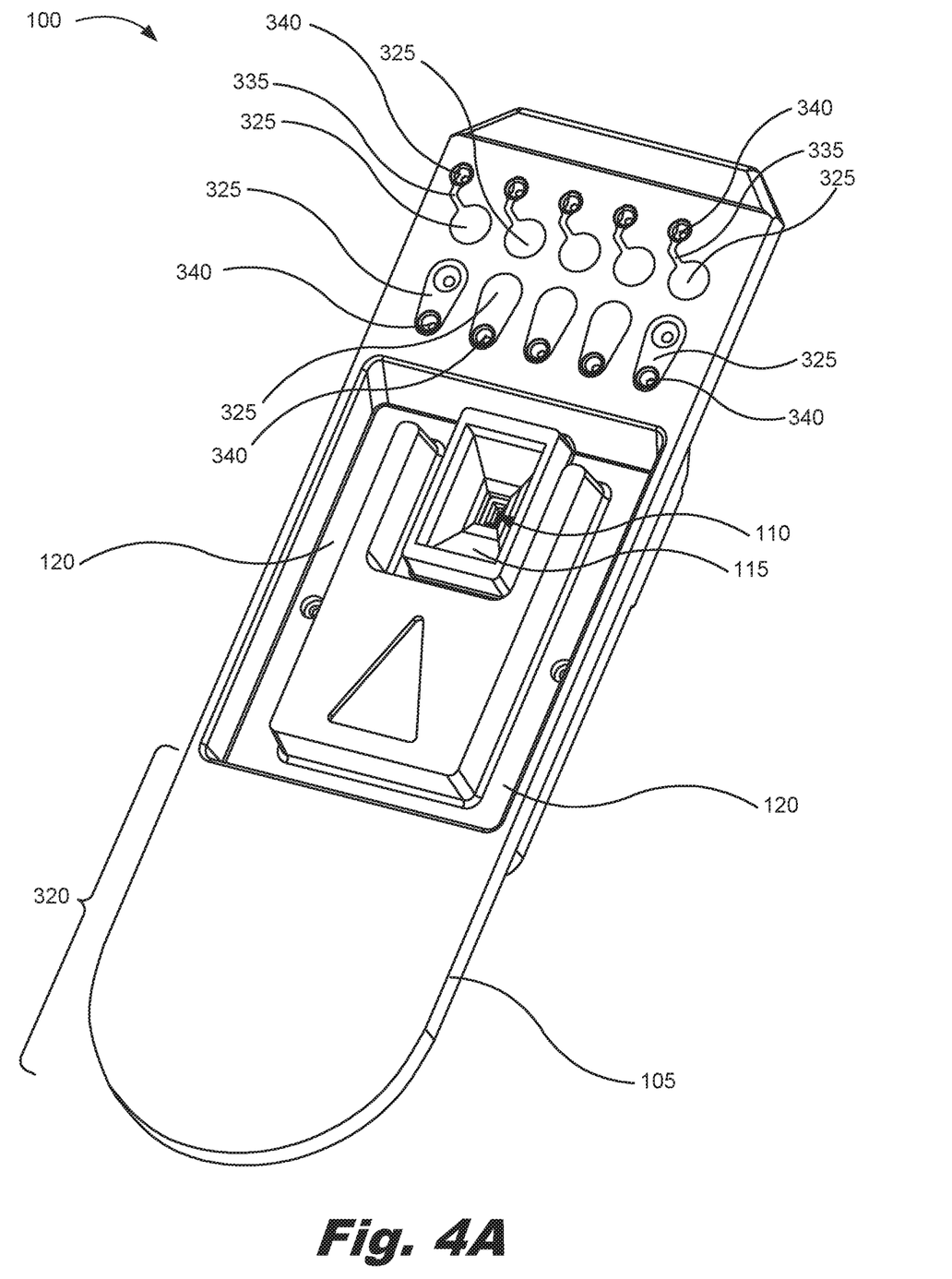
FIGS. 4A and 4B are front and rear perspective views, respectively, of a cassette according to a number of examples described herein.
Figure 4B:
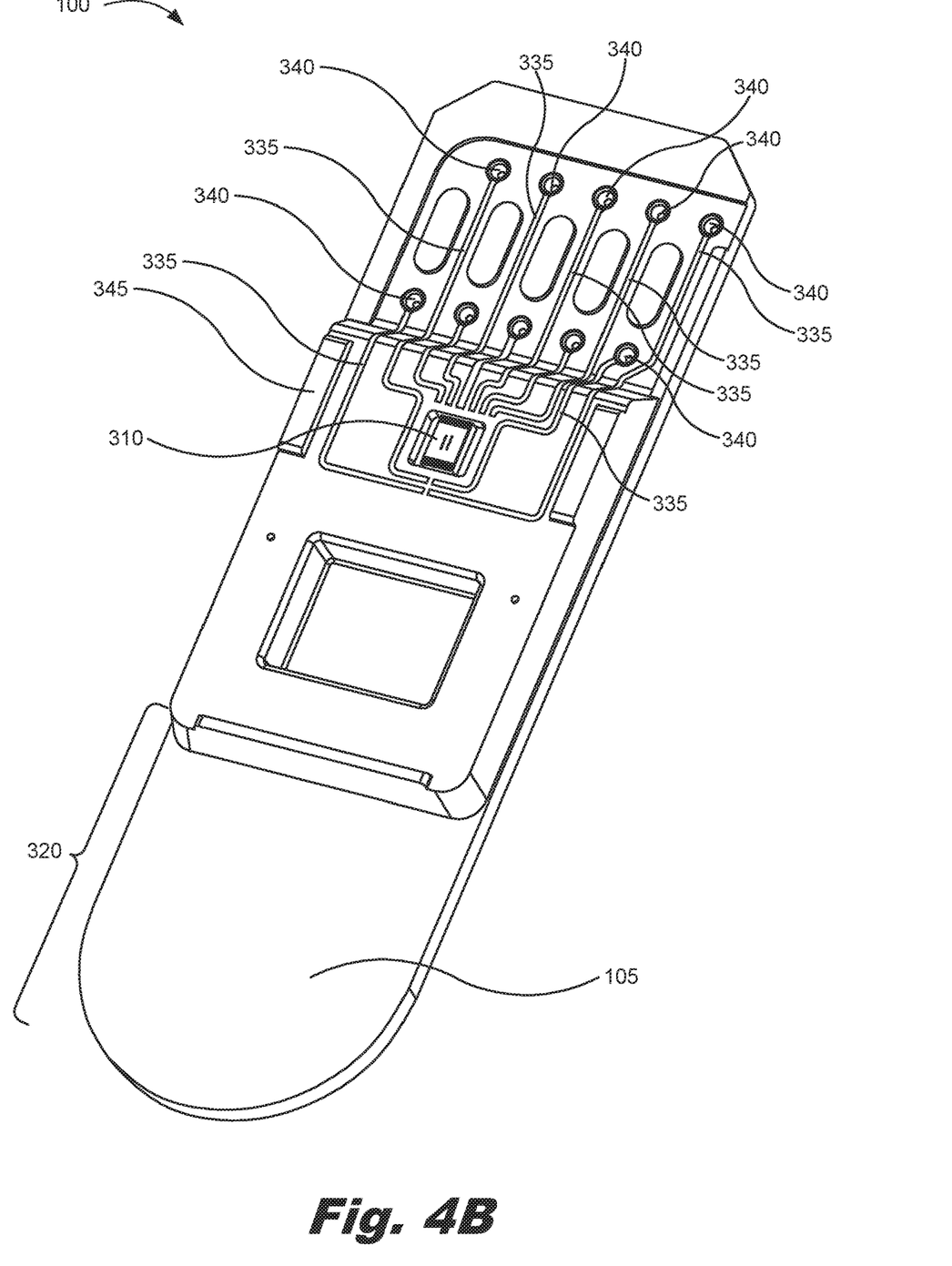

FIGS. 4A and 4B are front and rear perspective views, respectively, of a cassette (100) according to a number of examples described herein. As described above, the cassette (100) includes a substrate (105), a die (110) coupled to the substrate (105), and a reservoir (115) defined in the substrate (105) and an overflow reservoir (120) defined around a perimeter of the reservoir (115). The cassette (100) with its substrate (105), die (110), reservoir (115), and overflow reservoir (120) may be similar to that cassette (FIG. 1, 100) as described in connection with FIG. 1.

The substrate (105) may be formed to allow a user to insert or otherwise interface the cassette (100) with a system for ejecting a fluid into an assay such as the automated fluid ejection system described herein. In the example show in FIGS. 4A and 4B, the substrate (105) may include a handle (320). The handle (320) allows a user to grip the cassette (100) in order to manipulate the cassette (100) and place the cassette (100) into the system used to eject a fluid into an assay.

The cassette (100) may further include a number of connection pads (325) and electrical traces (330) so that the die (110) of the cassette (100) can receive electrical signals directing when, where, and how to eject an amount of fluid therefrom. In an example, the cassette (100) is moved relative to an assay plate positioned below the cassette (100) such that placement of the die (110) over any portion of the assay plate and ejection of fluid from the die (110) allows an amount of fluid to be ejected into any number of wells formed in the assay plate. The ejection of the fluid from the die (110) is directed by a controller of the automated fluid ejection system as described herein.

Thus, in order to allow the cassette (100) to interface with the system for ejecting a fluid into an assay, the cassette (100) may include a number of contact pads (325) that interface with, for example, a number of pogo connectors on a printed circuit assembly (RCA) of the automated fluid ejection system. In the examples shown in the figures of the present description, the number of contact pads (325) is ten. However, the present specification contemplates the use of less or more contact pads (325). The number of contact pads (325) may be varied among different examples because the die (110) may receive signals from the RCA directing a number of microelectromechanical systems (MEMS) devices to be activated. Consequently, more or less contact pads (325) may be added or subtracted from those shown in FIGS. 4A and 4B based on the number of signals used to activate any number of MEMS devices within the die (110). Not all of the contact pads (325) have been indicated in FIGS. 4A and 4B in order to allow for better understanding of the cassette (100).

In an example, a number of traces (335) may electrically couple each of the contact pads (325) to a via (340). In other examples the contact pads (325) themselves may be electrically coupled to their respective vias (340) without the use of traces (335).

In an example, the contact pads (325) and traces (335) may be formed onto the surface of the substrate (105) using a LDS process. Again, during the LDS process, the non-conductive, metallic, inorganic compounds are activated by a laser providing a surface into which a layer of conduct metal may be deposited using, for example, an electroless copper bath. The vias (340) may provide an electrical connection to a number of other traces (335) formed on an opposite side of the cassette (100).

FIG. 4B is a back, perspective view of the cassette (100) of FIG. 4A according to an example of the principles described herein. The vias (340) provide an electrical connection between the contact pads (325) on the front side of the cassette (100) to a number of traces (335) defined on the back side (345) of the cassette (100). These traces (335) electrically couple each of the vias (340) to at least one die pad defined on the die (110). In this manner, a PCA may interface with the contact pads (325) defined on the front of the cassette (100) in order to send electrical signals to the die (110) to cause the die (110) to, at least, eject an amount of fluid therefrom.

As described herein, the cassette (100) of FIGS. 4A and 4B includes a reservoir (115). The reservoir (115), in this example, may generally be in the form of a funnel shape such that a user, during operation, may provide an amount of fluid therein. The funnel shape of the reservoir (115) may funnel the fluid to a slot defined above a proximal side of the die (110). Thus, the funnel shaped reservoir (115) as shown in FIGS. 4A and 4B, may provide a constant supply of fluid to the die (110) using gravitational forces. To prevent the fluid from contacting the contact pads (325) on the front side of the cassette (100) and/or a number of traces (335) defined on the front or back side of the cassette (100), the overflow reservoir (120) may be disposed between the reservoir (115) and those contact pads (325) and/or number of traces (335). In the example shown in FIG. 4A, the overflow reservoir (120) is in the form of a moat around the entire perimeter of the reservoir (115). During operation, if a user were to pipette an amount of fluid into the reservoir (115) that exceeded the volumetric capacity of the reservoir (115), the fluid will flow into the overflow reservoir (120) before flowing at or around the contact pads (325) and/or number of traces (335). Consequently, the electrical connections provided by the contact pads (325) and/or number of traces (335) will not be shorted out by the fluid and the die (110) and automated assay fluid dispensing system will not be damaged.

Figure 5:
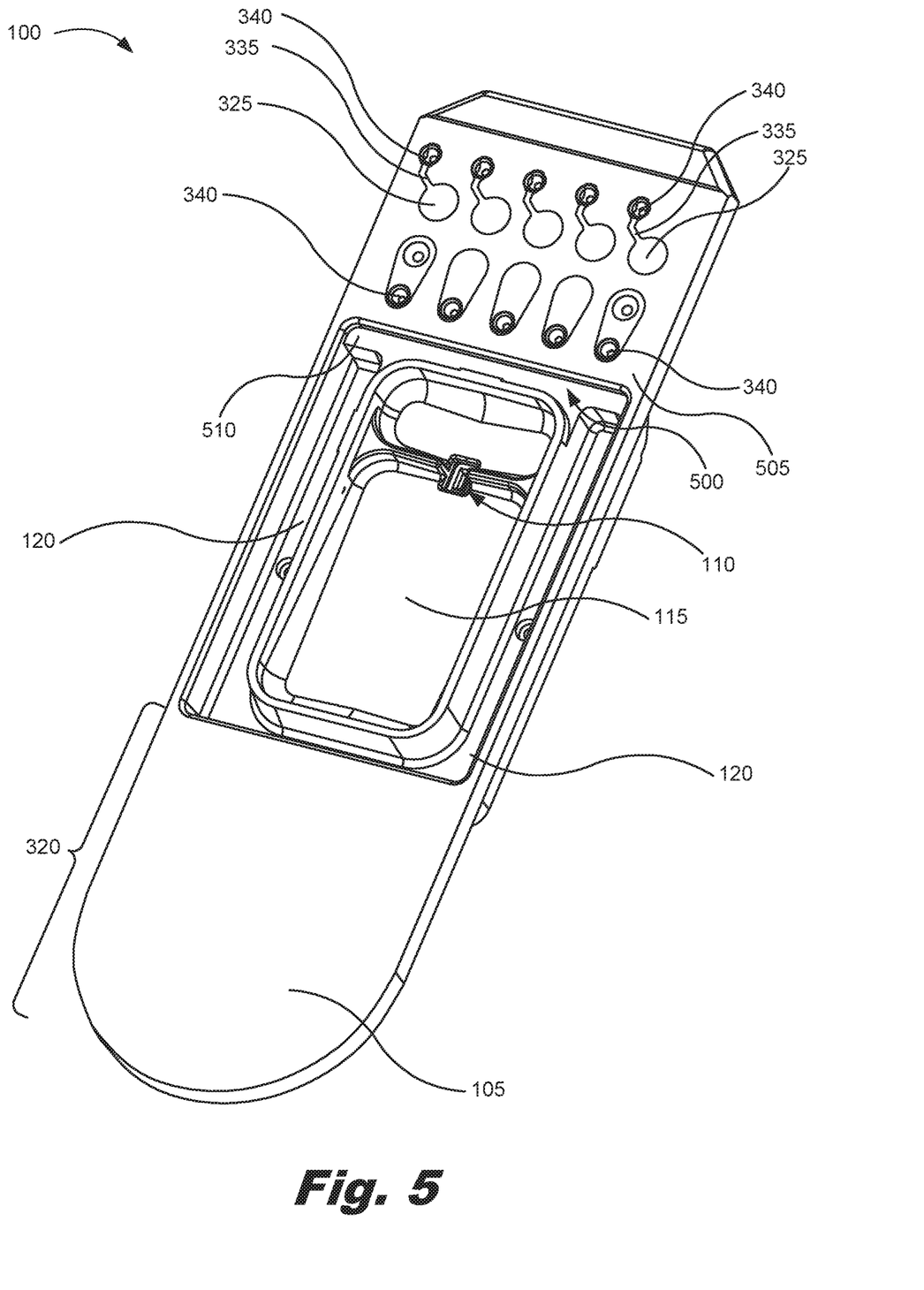
FIG. 5 is a front perspective view of a cassette according to an example of the principles described herein.

FIG. 5 is a front perspective view of a cassette (100) according to an example of the principles described herein. A back, perspective view of the cassette (100) of FIG. 5 may be similar to form as FIG. 4B and will not be described now. Similar to FIG. 4A, the cassette (100) may include a substrate (105), a die (110) coupled to the substrate (105), and a reservoir (115) defined in the substrate (105) and an overflow reservoir (120) defined around a perimeter of the reservoir (115). In this example, the reservoir (115) may be relatively larger than the reservoir (115) shown in FIG. 4A. Additionally, the overflow reservoir (120) may not be defined in the substrate (105) to extend completely around the entire perimeter of the reservoir (115). Instead, in this example, the overflow reservoir (120) extends around three sides of the reservoir (115). However, as can be seen in FIG. 5, a wall (500) may be formed in the substrate (105) that serves as a fluidic break between the reservoir (120) and the contact pads (325) and/or number of traces (335). This wall (500) may be formed as a result of the relative depths of the reservoir (115)/overflow reservoir (120) as compared to an upper-most surface (505) of the substrate (105). In this example, a lip (510) may be present around at least a portion of the perimeter of the reservoir (115) that introduces two-tier level system: the first level defining the lowest point in the bottom of the reservoir (115) and overflow reservoir (120) and the second level defining the lip (510) formed around a perimeter of both the reservoir (115) and overflow reservoir (120).

Figure 6:
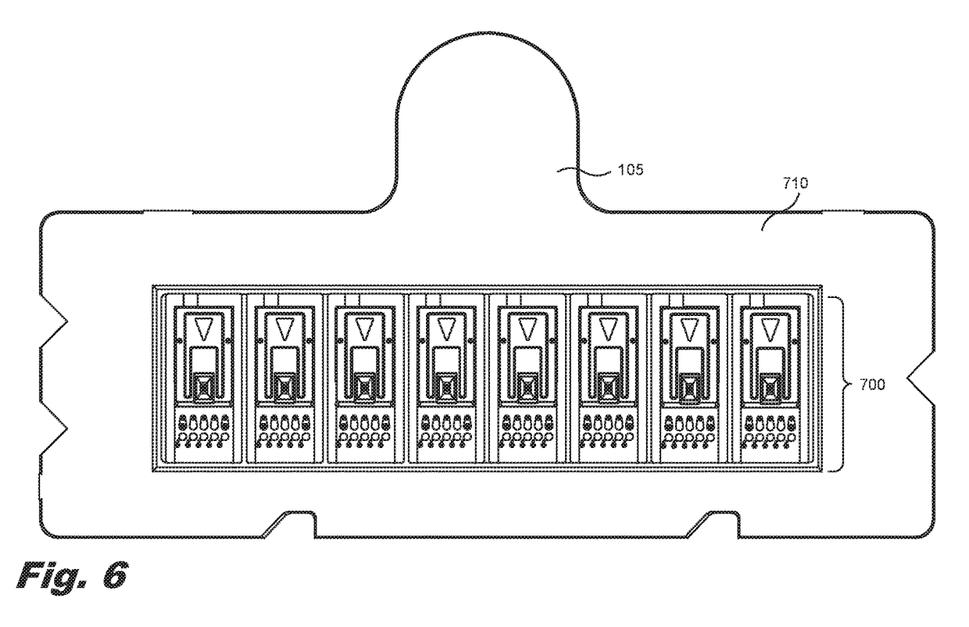
FIG. 6 is a front plan view of a number of dispense head assemblies formed in a substrate according to an example of the principles described herein.

FIG. 6 is a front plan view of a number of dispense head assemblies (700) formed in a substrate (105) according to an example of the principles described herein. Each of the dispense head assemblies (700) may be placed within the substrate (105) and may include a die (110), reservoir (115), contact pads (325), vias (340), traces (335), as described herein in connection with FIGS. 4A and 4B. In the example shown in FIG. 5, the dispense head assemblies (700) are mounted onto a frame (510). In an example, the dispense head assemblies (500) may be mechanically coupled to the frame (710) by, for example, a number of clips. In an example, the frame (710) forms the substrate (105) of each of the dispense head assemblies (700) such that each of the dispense head assemblies (700) are formed into a single monolithic frame (710).

The specification and figures describe a cassette that includes, among other devices, an overflow reservoir that prevents an amount of fluid from contacting contact pads and/or a number of electrical traces defined on the surface of the cassette. The overflow reservoir may be formed such that a superfluous amount of fluid pipetted into a reservoir may overflow into the overflow reservoir before contacting the contact pads and/or number of electrical traces. This prevents shorting out of a die or automated assay fluid dispensing system. Consequently, damage to these parts may be reduced.

The preceding description has been presented to illustrate and describe examples of the principles described. This description is not intended to be exhaustive or to limit these principles to any precise form disclosed. Many modifications and variations are possible in light of the above teaching.

What is claimed is:

1. A cassette comprising:
   a substrate;
   a die coupled to the substrate;
   a reservoir defined in a first side of the substrate exposing a proximal side of the die to an external atmosphere, the reservoir being divided into multiple compartments; and
   an overflow reservoir defined in the first side of the substrate and surrounding at least a portion of a perimeter of the reservoir.

2. The cassette of claim 1, wherein the overflow reservoir surrounds the entire perimeter of the reservoir, a wall separating the reservoir and overflow reservoir running around the entire perimeter of the reservoir.

3. The cassette of claim 1, wherein the cassette further comprises a number of electrical contacts to interface with an electrical dispensing device and wherein the overflow reservoir is disposed between the reservoir and the electrical contacts.

4. The cassette of claim 3, wherein a wall is defined between the overflow reservoir and the electrical contacts.

5. The cassette of claim 1, wherein a volume of the overflow reservoir is between 130 and 220 μL.

6. The cassette of claim 1, wherein the substrate, reservoir, and overflow reservoir are a formed from a monolithic piece of material.

7. A system comprising the cassette of claim 1, the system comprising:
   at least one dispense head, the at least one dispense head comprising the cassette; and
   a number of electrical contacts formed on the first side of the substrate.

8. The system of claim 7, wherein the overflow reservoir surrounds the entire perimeter of the reservoir.

9. The system of claim 7, wherein the at least one dispense head further comprises a number of electrical contacts to interface with an electrical dispensing device and wherein the overflow reservoir is placed between the reservoir and the electrical contacts.

10. The system of claim 9, wherein a wall is defined between the overflow reservoir and the electrical contacts.

11. The cassette of claim 1, wherein the substrate, reservoir, and overflow reservoir are a formed from a monolithic piece of thermoplastic material.

12. A micro electromechanical system (MEMs) device, comprising:
- a substrate having a first side and a second side;
  - a die coupled to the second side of the substrate;
  - a reservoir defined within a first side of the substrate exposing a proximal side of the die to an external atmosphere; and
  - an overflow reservoir defined in the first side of the substrate and surrounding at least multiple sides of a perimeter of the reservoir.

13. The MEMS device of claim 12, further comprising a number of electrical contacts to interface with an electrical dispensing device and wherein the overflow reservoir is placed between the reservoir and the electrical contacts.

14. The MEMS device of claim 12, wherein a volume of the overflow reservoir is between 180 and 260 µL.

15. The MEMS device of claim 12, wherein the overflow reservoir surrounds the entire circumference of the reservoir.

16. The cassette of claim 1, a portion of the substrate extending to form a handle.

17. The cassette of claim 1, further comprising a plurality of contact pads electrically connected by traces with the die.

18. The cassette of claim 1, wherein the overflow reservoir extends on three sides of the reservoir.

19. The cassette of claim 1, further comprising a lip around at least a portion of a perimeter of the reservoir.

20. The cassette of claim 1, further comprising a lip around a perimeter of both the reservoir and the overflow reservoir.

* * * * *